US010401001B2

(12) United States Patent
Kennedy et al.

(10) Patent No.: US 10,401,001 B2
(45) Date of Patent: Sep. 3, 2019

(54) DISPOSABLE LIGHT SOURCE FOR AN ENDOSCOPE OR RETRACTOR

(71) Applicant: Sunoptic Technologies LLC, Jacksonville, FL (US)

(72) Inventors: David T Kennedy, Jacksonville, FL (US); Brandon M Closson, Saint Johns, FL (US)

(73) Assignee: Sunoptic Technologies LLC, Jacksonville, FL (US)

( * ) Notice: Subject to any disclaimer, the term of this patent is extended or adjusted under 35 U.S.C. 154(b) by 22 days.

(21) Appl. No.: 15/591,241

(22) Filed: May 10, 2017

(65) Prior Publication Data

US 2018/0328572 A1 Nov. 15, 2018

(51) Int. Cl.
| | | |
|---|---|---|
| *F21V 17/00* | (2006.01) | |
| *F21L 4/00* | (2006.01) | |
| *G02B 23/24* | (2006.01) | |
| *A61B 1/06* | (2006.01) | |
| *A61B 1/00* | (2006.01) | |
| *F21V 23/04* | (2006.01) | |
| *A61B 1/32* | (2006.01) | |
| *F21W 131/20* | (2006.01) | |

(52) U.S. Cl.
CPC ........ *F21V 17/002* (2013.01); *A61B 1/00105* (2013.01); *A61B 1/06* (2013.01); *A61B 1/0684* (2013.01); *F21L 4/00* (2013.01); *G02B 23/2469* (2013.01); *G02B 23/2476* (2013.01); *A61B 1/32* (2013.01); *F21V 23/0414* (2013.01); *F21W 2131/20* (2013.01)

(58) Field of Classification Search
CPC ..... A61B 1/07; A61B 1/0684; A61B 1/00062; A61B 1/0669; A61B 1/06; G02B 23/2469; G02B 23/2476; G02B 6/0008; G02B 23/26; F21V 23/0414; F21L 4/00; F21L 4/027
See application file for complete search history.

(56) References Cited

U.S. PATENT DOCUMENTS

| 4,551,028 A | 11/1985 | Rowen et al. |
| 5,161,250 A | 11/1992 | Ianna et al. |
| 6,428,180 B1 | 8/2002 | Karrum et al. |

(Continued)

OTHER PUBLICATIONS

International Search Report and Written Opinion of the ISA for corresponding International PCT Application No. PCT/US2018/031762.

*Primary Examiner* — Peggy A Neils
(74) *Attorney, Agent, or Firm* — Howson & Howson LLP

(57) ABSTRACT

A portable light source unit for being coupled to an instrument is provided. The unit includes a housing having a port for receiving a light guide end tip of the instrument, a battery and LED mounted within the housing, and a pull tab that extends through the housing and electrically isolates the LED from the battery. Upon removal of the pull tab, an electrical connection is completed between the battery and the LED. The unit also includes driver circuitry for the LED ensuring that a constant level of current is provided to the LED so that the LED produces light of a constant brightness. The driver circuitry also produces a current spike for breaking an inline fuse when a remaining charge of the battery is unable to provide a voltage at the constant level of current above a pre-determined threshold level thereby de-energizing the LED.

11 Claims, 5 Drawing Sheets

(56) References Cited

U.S. PATENT DOCUMENTS

| | | | | |
|---|---|---|---|---|
| 6,591,049 | B2 * | 7/2003 | Williams | G02B 6/0008 385/123 |
| 6,595,676 | B2 * | 7/2003 | Starry | F21L 4/005 362/196 |
| 7,631,981 | B2 | 12/2009 | Miller et al. | |
| 7,758,203 | B2 * | 7/2010 | McMahon | A61B 1/303 362/183 |
| 7,802,910 | B2 * | 9/2010 | Middlemass | G02B 6/4298 362/555 |
| 8,283,877 | B2 * | 10/2012 | Lenk | H05B 33/0815 315/209 R |
| 8,388,523 | B2 * | 3/2013 | Vivenzio | A61B 1/00105 362/574 |
| 8,905,573 | B2 * | 12/2014 | Sharrah | F21L 4/005 362/205 |
| 2007/0247867 | A1 | 10/2007 | Hunter et al. | |
| 2009/0097236 | A1 | 4/2009 | Miller et al. | |
| 2011/0184239 | A1 * | 7/2011 | Wright | A61B 1/00016 600/118 |
| 2014/0275790 | A1 | 9/2014 | Vivenzio et al. | |
| 2014/0293590 | A1 | 10/2014 | Pathy | |
| 2016/0310121 | A1 | 10/2016 | Swift | |

* cited by examiner

DISPOSABLE LIGHT SOURCE FOR AN ENDOSCOPE OR RETRACTOR

BACKGROUND

The present invention relates to a light source for instruments used to illuminate a surface or cavity, and more particularly, the present invention relates to a portable, disposable (i.e., single use) or reusable (i.e., capable of being sterilized) light source for such instruments.

Endoscopes, lighted retractors, and like instruments may be used in a hospital, health care facility, or the like, for instance, to illuminate a cavity or surface of a patient. Such instruments are typically attached to a stationary light source unit that remains in one location during use or is fastened to a rolling cart or the like and that transmits light to the instrument via a fiber optic cable that tethers the instrument to the stationary light source unit. This conventional arrangement can be inconvenient and cumbersome during use. For instance, this arrangement necessarily requires the operator to manage a cumbersome light source cart within limited available space and relatively heavy and cumbersome fiber optic cables. In addition, the cables and related equipment must be subjected to expensive and time consuming sterilization processes between each use.

SUMMARY

According to an embodiment, a portable light source unit adapted for being coupled to an instrument is provided. The unit includes a housing having a port for receiving and retaining an end tip of a light guide of the instrument, a light source comprising a light emitting diode mounted within the housing, and a battery mounted within the housing for powering the light emitting diode. An activation pull tab extends through the housing and electrically isolates the light source from the battery and, upon removal from the housing, enables an electrical connection to be completed between the battery and the light source.

Some contemplated embodiments of the unit further include driver circuitry for the light emitting diode. The driver circuitry has an inline fuse and ensures that a constant level of current is provided to the light emitting diode after the pull tab has been removed from the light source unit so that the light emitting diode produces light at a constant brightness. The driver circuitry may be configured to automatically produce a current spike for breaking the inline fuse when a remaining charge of the battery is unable to provide a voltage at the constant level of current above a pre-determined threshold level thereby de-energizing the light emitting diode and preventing further use of the light source unit.

According to another aspect of an embodiment, a method of providing an instrument with a source of light is provided. The method includes coupling a portable light source unit provided in a sterile condition to an end tip of a light guide of an instrument such that the light source unit is supported and carried on the instrument. The method also requires a pull tab to be manually removed from the light source unit to energize a light source housed within the light source unit. The light source unit includes a housing having a port for receiving the end tip of the light guide of the instrument, and the light source comprises a light emitting diode that is mounted within the housing. A battery is mounted within the housing for powering the light emitting diode. The pull tab extends through the housing and prevents electrical connection to be completed between the battery and the light source and, upon removal from the housing, enables electrical connection to be completed between the battery and the light source.

The light source unit may further include driver circuitry for the light emitting diode. The driver circuitry has an inline fuse and ensures that a constant level of current is provided to the light emitting diode after the pull tab has been removed from the light source unit so that the light emitting diode produces light at a constant brightness. The driver circuitry is configured to cause a current spike for breaking the inline fuse when a remaining charge of the battery is unable to provide a voltage at the constant level of current above a pre-determined threshold level. Breaking of the inline fuse de-energizes the light emitting diode and prevents further use of the light source unit.

BRIEF DESCRIPTION OF THE DRAWINGS

The features and advantages of the present invention should become apparent from the following description when taken in conjunction with the accompanying drawings, in which.

DETAILED DESCRIPTION

Figure 1A:
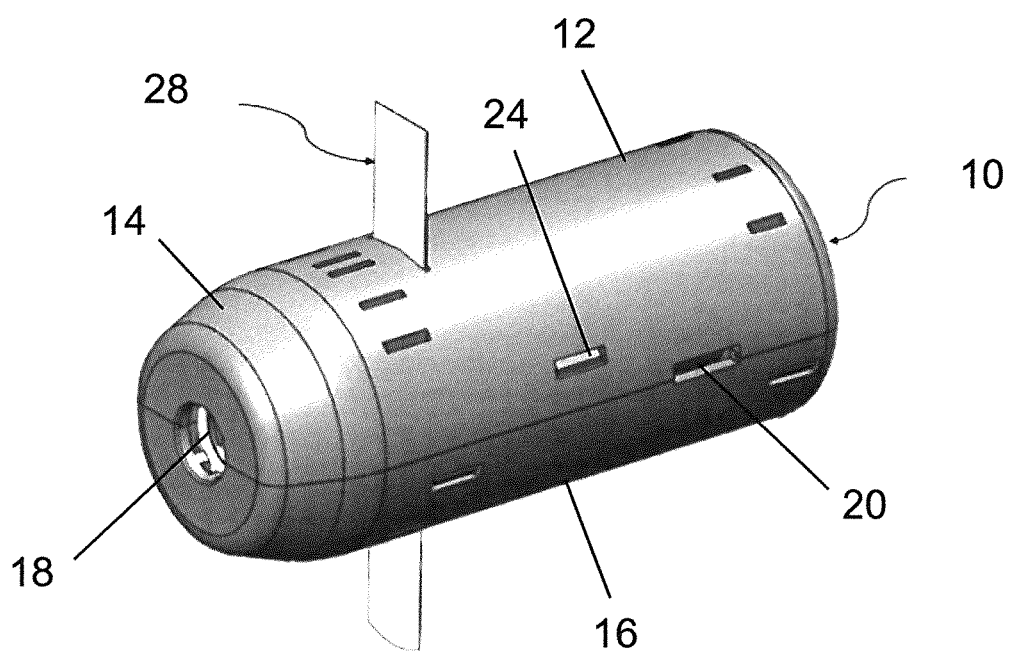
FIG. 1A is a perspective view of a portable light source unit according to an embodiment.

According to an embodiment, a portable, lightweight, single-use, readily disposable light source unit is provided that is adapted to be readily coupled to and decoupled from an end tip of a light post or guide of an endoscope, lighted retractor, or like medical or other instrument. The portable, disposable light source unit is intended to replace the conventional stationary light source and cable system described above. Thus, the light source unit couples directly to the instrument and is supported and carried thereby without the need for carts, outer support components, cables, tethers, fiber optic cables, or the like. The light source unit may be packaged and provided to an end user in a sterile condition. Alternatively, depending upon intended use of the light source unit, the product may be provided in a non-sterile condition.

According to an embodiment, the portable light source unit includes a battery powered light source, such as a light emitting diode (LED), activated by a removable pull tab. In the initial condition of the light source unit, the pull tab extends within and through the light source unit and prevents the light source from being electrically connected to and energized by a power source or battery. A part of the pull tab extends exteriorly of the light source unit and includes an end that may be gripped by a user. After the pull tab is gripped and intentionally withdrawn from the light source unit by an operator, the light source within the unit becomes electrically connected to the battery and is thereby activated and energized for purposes of emitting light.

Upon activation, the light source may emit white light for a certain amount of time until the light source unit automatically de-energizes the light source. According to a first embodiment, the light source unit may not include an on/off switch. According to an alternate embodiment, the light source unit may include an on/off switch enabling the LED to be manually powered off and on by the end user after the pull tab has been removed.

A circuit may be contained within the light source unit that automatically de-energizes the light source when a level of power or life remaining in the battery is reduced to or below a threshold level. According to some contemplated embodiments, after the light source is deactivated, a new light source unit can be applied and the deactivated unit may be disposed, recycled, returned to the manufacturer, or the like.

The light source unit may be originally packaged and provided to the end user in a sterile condition. This relieves the end-user from needing to ensure sterility of the unit before use. After use, the light source unit may be disposed according to local regulations. To conform to the different possibilities that must be considered for complying with many different regulations, one or more small apertures may be provided in the housing of the light source unit to enable the unit to be manually broken apart after use, for instance, for battery removal purposes, or like task. As an alternate embodiment, the light source unit may be provided in a non-sterile condition, depending upon intended end use.

Figure 1B:
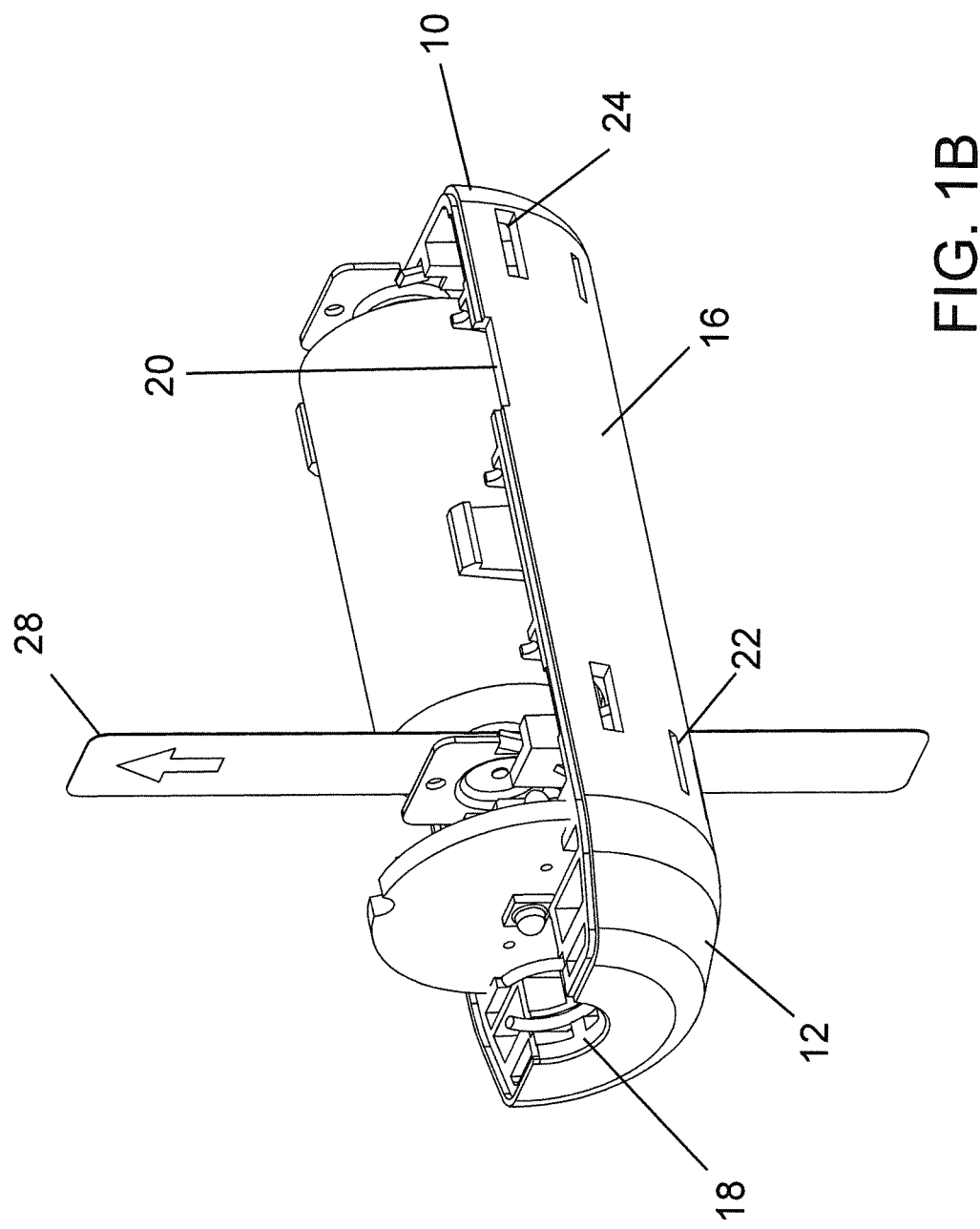
FIG. 1B is a perspective view of the portable light source unit of FIG. 1A with a part of the housing removed.

According to an embodiment as shown in FIGS. 1A and 1B, the light source unit 10 has a housing 12 that may include opposite molded so-called half shells, 14 and 16 (only one half of the housing is shown in FIG. 1B). Each half shell of the housing 12 may be made of plastic, such as food grade Acrylonitrile-Butadiene-Styrene (ABS), and may be assembled with the opposite half shell to form the complete housing 12. In some embodiments, the half shells may be identical and may be snap-fitted together (i.e., for instance, with resilient fingers or the like that latch within opposing depressions or the like). According to other embodiments, each of the half shells may be of a unique design (i.e., not identical).

The housing 12 defines a port 18 in one end of the light source unit 10 adapted to receive and couple to a light post of an endoscope, retractor, medical instrument, or other like instrument. The housing 12 may also include at least one aperture 20 for use in separating the half shells to access and properly dispose of the battery or other components after use. For instance, a tip of a screw driver or the like may be inserted into the aperture 20 to pry open the half shells comprising the housing 12. In addition, the housing 12 may include ventilation apertures 22 and may also include connection apertures 24 for use in permitting the half shells to snap together (i.e., via resilient latching fingers or the like) and becoming locked in a closed condition.

The housing 12 also defines slots 26 in each half shell for accommodating the activation pull tab 28. FIGS. 1A and 1B show the condition of the pull tab 28 extending through the light source unit 10 as initially provided to an end-user. In this condition, the light source within the housing 12 is de-energized and no light is being emitted since the pull tab 28 prevents the light source from being powered by a battery. The pull tab 28 may extend outwardly from one or both sides of the housing 12 to provide an end of the pull tab 28 which may be readily gripped by the end-user when activation of the light source is desired. Thus, if the pull tab 28 is gripped and pulled out of the housing 12, the light source becomes energized and begins to emit light.

Figure 2:
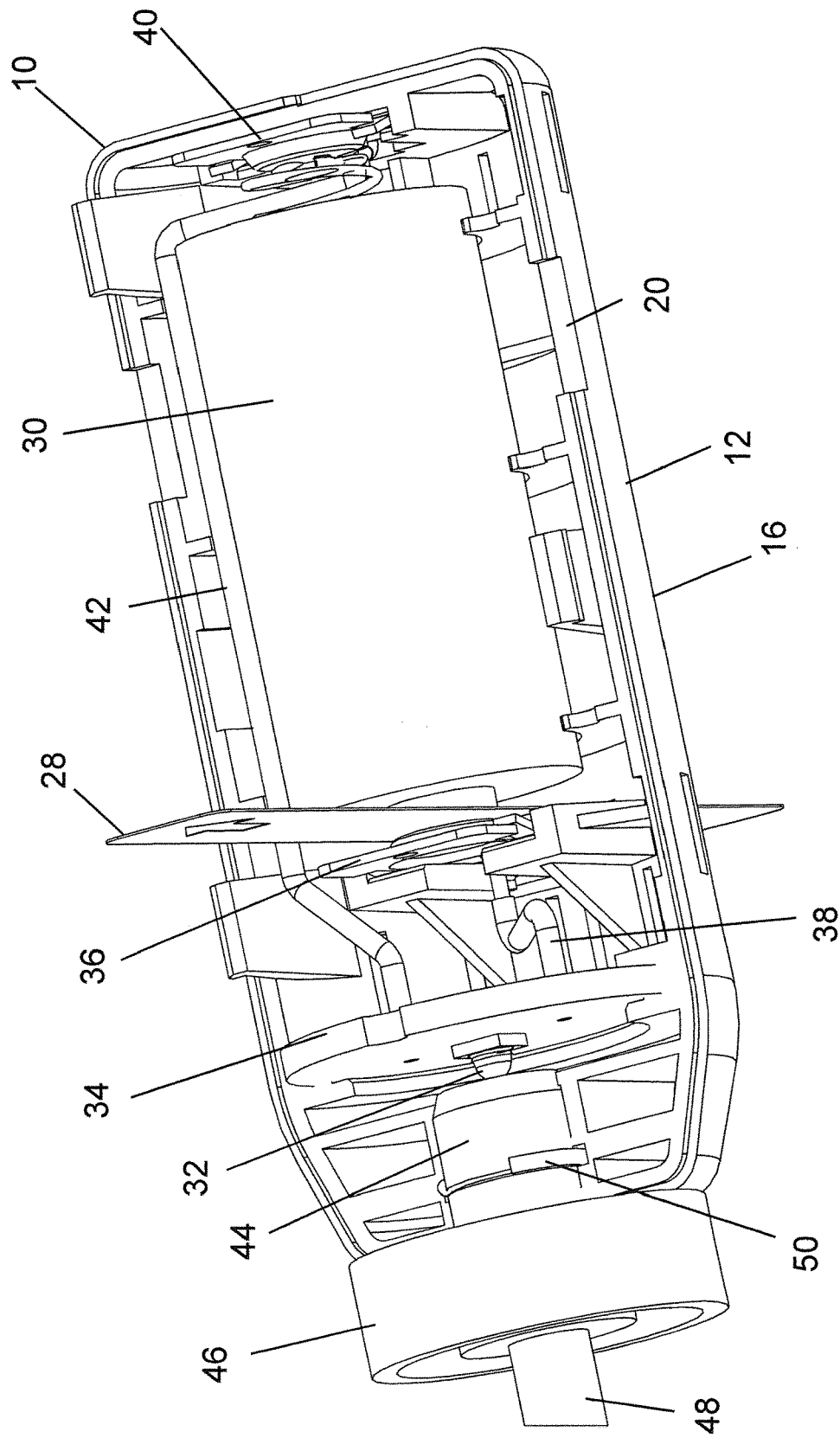
FIG. 2 is a perspective view of a portable light source unit with a part of the housing removed and with the portable light source coupled to an end tip of a retractor according to an embodiment.
Figure 3:
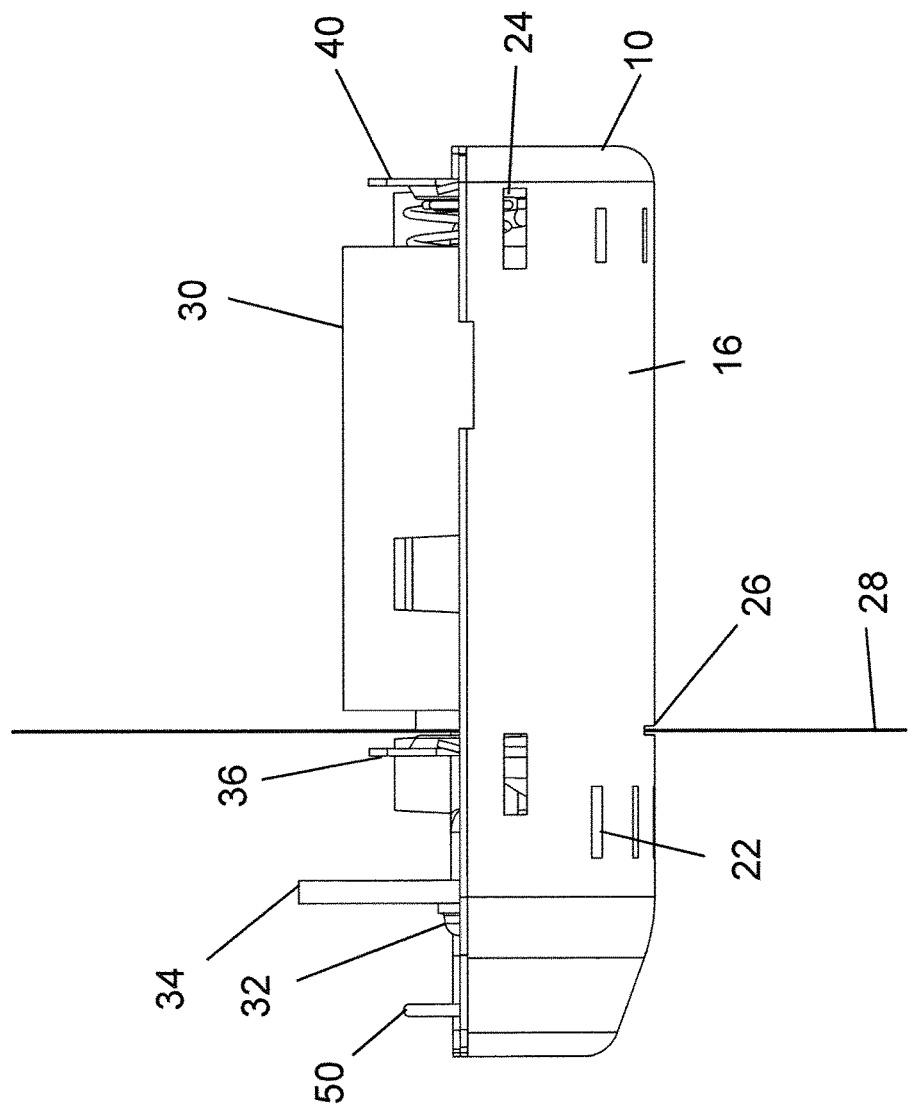
FIG. 3 is an elevational view of the portable light source unit with a part of the housing removed according to an embodiment.

Solely for purposes of explanation, FIGS. 1B, 2 and 3 show the light source unit 10 with one of the half shells of the housing 12 removed. The housing 12 houses a battery 30 which may be a lithium metal primary cell battery or other type of battery and a light emitting diode (LED) 32 mounted on a drive printed circuit board assembly (PCBA) 34. The drive PCBA 34, and thus LED 32, is electrically connected to the battery 30 via a positive battery contact 36 and conductor 38 which connects the positive battery contact 36 to the drive PCBA 34 and via a negative spring battery contact 40 and conductor 42 which connects the negative spring battery contact 40 to the drive PCBA 34.

In the initially provided condition of the light source unit, the non-conductive pull tab 28 extends between the positive battery contact 36 and the battery 30 to electrically isolate the positive terminal of the battery 30 and the positive battery contact 36. However, when the pull tab 28 is removed by the end-user, the positive battery contact 36 directly engages the positive terminal of the battery 30 and completes the circuit to permit the LED 32 to be energized by the battery 30.

The end tip 44 of a separate instrument 46 is shown in FIG. 2. The end tip 44 includes a light post or light guide 48 that is inserted within the port 18 of the light source unit 10 and arranged therein in a position to receive light emitted from the LED 32. The light source unit 10 may include a spring clip 50 or the like designed to couple with a groove within the end tip 44 or light guide 48 of the instrument 46 to secure the light source unit 10 to the instrument 46 and prevent disengagement of the light post or light guide 48 from the port 18.

The drive PCBA 34 includes a boost topology LED driver and an inline fuse. The driver ensures that constant current of a predetermined level is provided to the LED 32 regardless of the charge remaining within the battery 30. Thus, a consistent, readily reproducible, and desired amount of light is provided by the light source unit 10 throughout its useful life. The inline fuse acts as a protection device against surge current events and is also utilized to de-energize the LED 32 at the end of useful life of the battery 30 as discussed below in greater detail.

After activation and continuous use for a period of time, the voltage provided by the battery 30 will become depleted to or below a threshold minimum voltage level. Upon depletion of the voltage supplied by the battery at the constant level of current to or below the threshold minimum voltage level, the driver will cause a current spike to be produced to break the inline fuse and open the circuit thereby cutting off power to the LED 32. The breaking of the inline fuse within the light source unit 10 prevents further use or re-use of the light source unit 10. For purposes of example, the current spike may occur at approximately 90 minutes after initial activation of the light source unit 10.

After the inline fuse breaks, the light source unit 10 may be disposed or recycled. In some cases, the housing 12 may be opened via pressure applied with a screwdriver of the like within the aperture 20 to enable battery removal before disposal of the unit. According to some contemplated embodiments, the light source unit 10 may not be designed for reuse (i.e., battery replacement). However, according to other contemplated embodiments, the light source may be capable of multiple uses via an optional on/off switch as discussed below.

Figure 4:
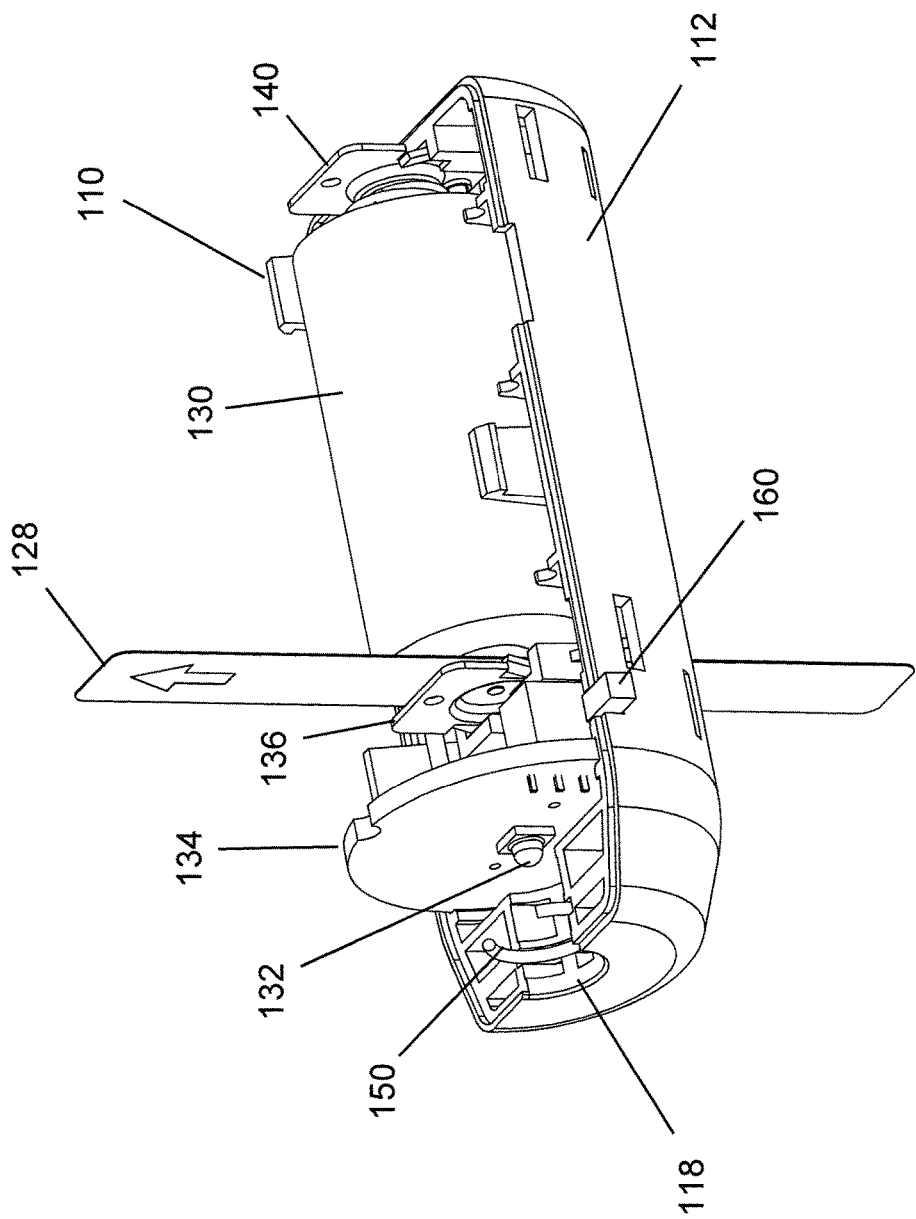
FIG. 4 is a perspective view of a second embodiment of a portable light source unit with a part of the housing removed according to an embodiment.

A second embodiment of a light source unit 110 is shown in FIG. 4. The light source unit 110 may include all or some of the features discussed above. For example, the light source unit 110 may include a housing 112, a port 118, a pull tab 128, a battery 130, a LED 132, a drive PCBA 134, battery contacts 136 and 140, and a spring clip 150. In addition, the light source unit 110 may also include an on/off switch 160 for manually switching on and off the light source unit 10 during lifetime of the battery 130. The light source unit 110 may be disposable and may include the on/off switch 160 for purposes of prolonging battery life, for instance, during a procedure requiring only intermittent use of the light source. Thus, after the pull tab has been removed from the unit, the on/off switch may be manipulated to power on or power off the LED.

Various modifications can be made to the light source units such as the type of light or electromagnetic radiation emitted by the LED, the activation method, the type and size of the battery or batteries, and the shape of the port used to couple to a light post or guide of a medical instrument. The light source unit may contain multiple or larger batteries that may provide higher or any desired level of milliampere hour (mAh) energy charge.

While a preferred portable light source unit capable of being removably coupled to an instrument has been described in detail, various modifications, alternations, and changes may be made without departing from the spirit and scope of the portable light source unit and instrument according to the present invention as defined in the appended claims.

The invention claimed is:

1. A method of providing an instrument with a source of light, comprising the steps of:
    coupling a portable, single use, light source unit to an end tip of a light guide of an instrument such that the light source unit is supported and carried on the instrument; and
    removing a pull tab from the light source unit to energize a light source housed within the light source unit;
    wherein the light source unit includes a housing having a port for receiving the end tip of the light guide of the instrument;
    wherein the light source comprises a light emitting diode that is mounted within the housing;
    wherein a battery is mounted within the housing for powering the light emitting diode;
    wherein the pull tab extends through the housing and prevents electrical connection to be completed between the battery and the light source and, upon removal from the housing, enables electrical connection to be completed between the battery and the light source; and
    wherein the light source unit includes driver circuitry for the light emitting diode, the driver circuitry having an inline fuse and ensuring that a constant level of current is provided to the light emitting diode after the pull tab has been removed from the light source unit so that the light emitting diode produces light at a constant brightness, and the driver circuitry causing a current spike for breaking the inline fuse when a remaining charge of the battery is unable to provide a voltage at the constant level of current above a pre-determined threshold level thereby de-energizing the light emitting diode and preventing further use of the light source unit.

2. The method according to claim 1, wherein the light source unit includes a spring clip contained within the housing for coupling the light source unit to the light guide of the instrument such that the end tip of the light guide of the instrument is located adjacent the light emitting diode.

3. The method according to claim 1, wherein the pull tab is made of a non-conductive material and extends between and electrically isolates a battery contact mounted within the housing and a battery terminal of the battery until the pull tab is removed from the housing.

4. The method according to claim 1, wherein the housing is made of two identical or unique half shells which are molded of plastic and snap-fit together.

5. The method according to claim 4, wherein the housing is made of food grade Acrylonitrile-Butadiene-Styrene (ABS).

6. The method according to claim 4, further comprising the steps of:
    removing the light source unit from the instrument after the inline fuse is broken and the light source unit discontinues emitting light; and
    prying the half shells apart to expose an interior of the light source unit to remove the battery.

7. The method according to claim 1, wherein the housing includes at least one slot through which the pull tab extends externally of the housing so that an end section of the pull tab is grippable externally of the housing and so that the pull tab may be pulled out of the housing during said removing step.

8. The method according to claim 1, wherein the battery is a lithium metal primary battery or comparable battery.

9. The method according to claim 1, wherein the instrument is selected from the group consisting of a medical instrument, a retractor, and an endoscope.

10. The method according to claim 1, wherein the light source unit includes an on/off switch and the method further comprises the step of toggling the on/off switch to power on or off the light emitting diode after the pull tab has been removed.

11. The method according to claim 1, further comprising the step of sterilizing the light source unit.

* * * * *